(12) United States Patent
Harshman et al.

(10) Patent No.: US 11,666,316 B2
(45) Date of Patent: Jun. 6, 2023

(54) WEIGHTED SURGICAL RETRACTOR SYSTEMS

(71) Applicants: Mayo Foundation for Medical Education and Research, Rochester, MN (US); Tara K. Phelps

(72) Inventors: Timothy A. Harshman, Jacksonville, FL (US); Raymond Phelps, Byron, MN (US); Steven Jurrens, Kasson, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 477 days.

(21) Appl. No.: 16/721,150

(22) Filed: Dec. 19, 2019

(65) Prior Publication Data

US 2020/0138425 A1 May 7, 2020

Related U.S. Application Data

(63) Continuation of application No. 15/122,504, filed as application No. PCT/US2015/018977 on Mar. 5, 2015, now abandoned.

(60) Provisional application No. 61/949,521, filed on Mar. 7, 2014.

(51) Int. Cl.
| | |
|---|---|
| *A61B 17/02* | (2006.01) |
| *A61B 90/35* | (2016.01) |
| *A61B 90/30* | (2016.01) |
| *A61B 1/32* | (2006.01) |
| *A61B 17/00* | (2006.01) |
| *A61B 90/50* | (2016.01) |

(52) U.S. Cl.
CPC ............... *A61B 17/02* (2013.01); *A61B 1/32* (2013.01); *A61B 90/30* (2016.02); *A61B 90/35* (2016.02); *A61B 2017/0046* (2013.01); *A61B 2017/00424* (2013.01); *A61B 2017/00477* (2013.01); *A61B 2017/00858* (2013.01); *A61B 2017/00876* (2013.01); *A61B 2017/00946* (2013.01); *A61B 2090/504* (2016.02)

(58) Field of Classification Search
CPC ..................................... A61B 17/02–17/0293
See application file for complete search history.

(56) References Cited

U.S. PATENT DOCUMENTS

| | | | |
|---|---|---|---|
| 3,227,156 A | 1/1966 | Gauthier | |
| 3,384,077 A | 5/1968 | Gauthier | |
| 3,542,015 A * | 11/1970 | Steinman | ............... A61B 17/02 600/206 |

(Continued)

*Primary Examiner* — Zade Coley
(74) *Attorney, Agent, or Firm* — Fish & Richardson P.C.

(57) ABSTRACT

This document provides surgical retractor devices and systems. For example, this document provides a weighted surgical retractor system. In one example embodiment, this document provides a weighted Deaver retractor system that includes a selectable amount of weight that can be releasably coupled to a shaft of the retractor. The surgical retractors provided herein can be used during a variety of surgical procedures, including surgical procedures performed on the abdomen, thoracic regions, limbs, and so on. In some embodiments, the surgical retractors provided herein are well-suited for retraction of the vaginal canal for hysterectomy surgery, and for other procedures for which vaginal retraction is necessary.

20 Claims, 8 Drawing Sheets

(56) References Cited

U.S. PATENT DOCUMENTS

| | | | |
|---|---|---|---|
| 3,709,215 A | | 1/1973 | Richmond |
| 3,783,873 A | * | 1/1974 | Jacobs ................ A61B 17/0206 606/208 |
| 5,984,867 A | * | 11/1999 | Deckman ........... A61B 17/0206 600/231 |
| 6,120,438 A | | 9/2000 | Rizvi |
| 6,280,379 B1 | * | 8/2001 | Resnick ................... A61B 1/32 600/220 |
| 6,302,842 B1 | * | 10/2001 | Auerbach .......... A61B 17/0206 600/219 |
| 6,464,634 B1 | | 10/2002 | Fraser |
| 6,979,291 B1 | | 12/2005 | Phillips et al. |
| 7,070,561 B1 | * | 7/2006 | Ansari ................... A61B 17/42 600/220 |
| 7,147,599 B2 | | 12/2006 | Phillips et al. |
| 7,384,393 B2 | | 6/2008 | Guinan |
| 7,396,329 B2 | | 7/2008 | Nakao |
| 7,481,766 B2 | | 1/2009 | Lee et al. |
| 2005/0099824 A1 | | 5/2005 | Dowling et al. |
| 2006/0149138 A1 | | 7/2006 | Fanous |
| 2008/0076968 A1 | * | 3/2008 | Bollier ................... A61B 17/02 600/227 |
| 2012/0116170 A1 | * | 5/2012 | Vayser ............... A61B 17/0218 600/245 |
| 2013/0190575 A1 | * | 7/2013 | Mast .................. A61B 17/7079 600/219 |
| 2013/0267786 A1 | * | 10/2013 | Vayser ................... A61B 17/02 600/213 |
| 2017/0071587 A1 | | 3/2017 | Harshman et al. |

* cited by examiner

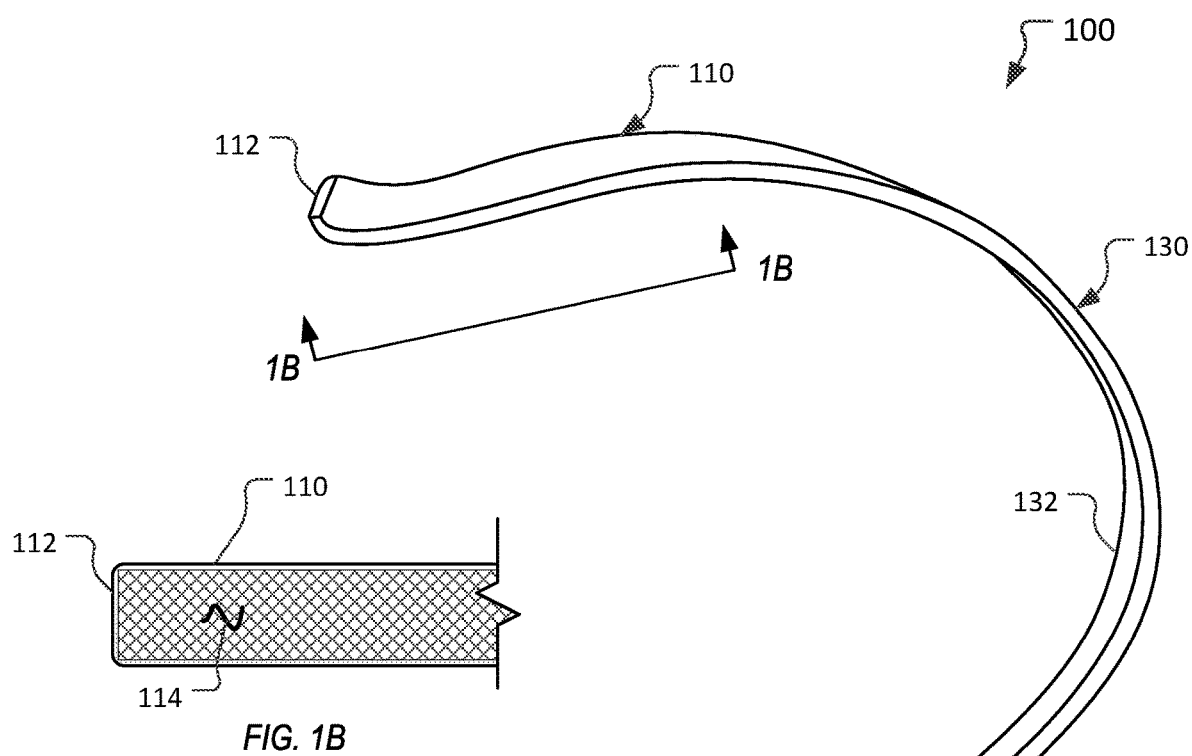
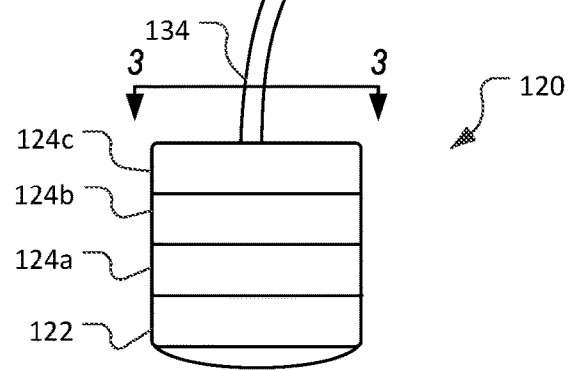
FIG. 1B
FIG. 1A

Section 3--3

Section 3--3

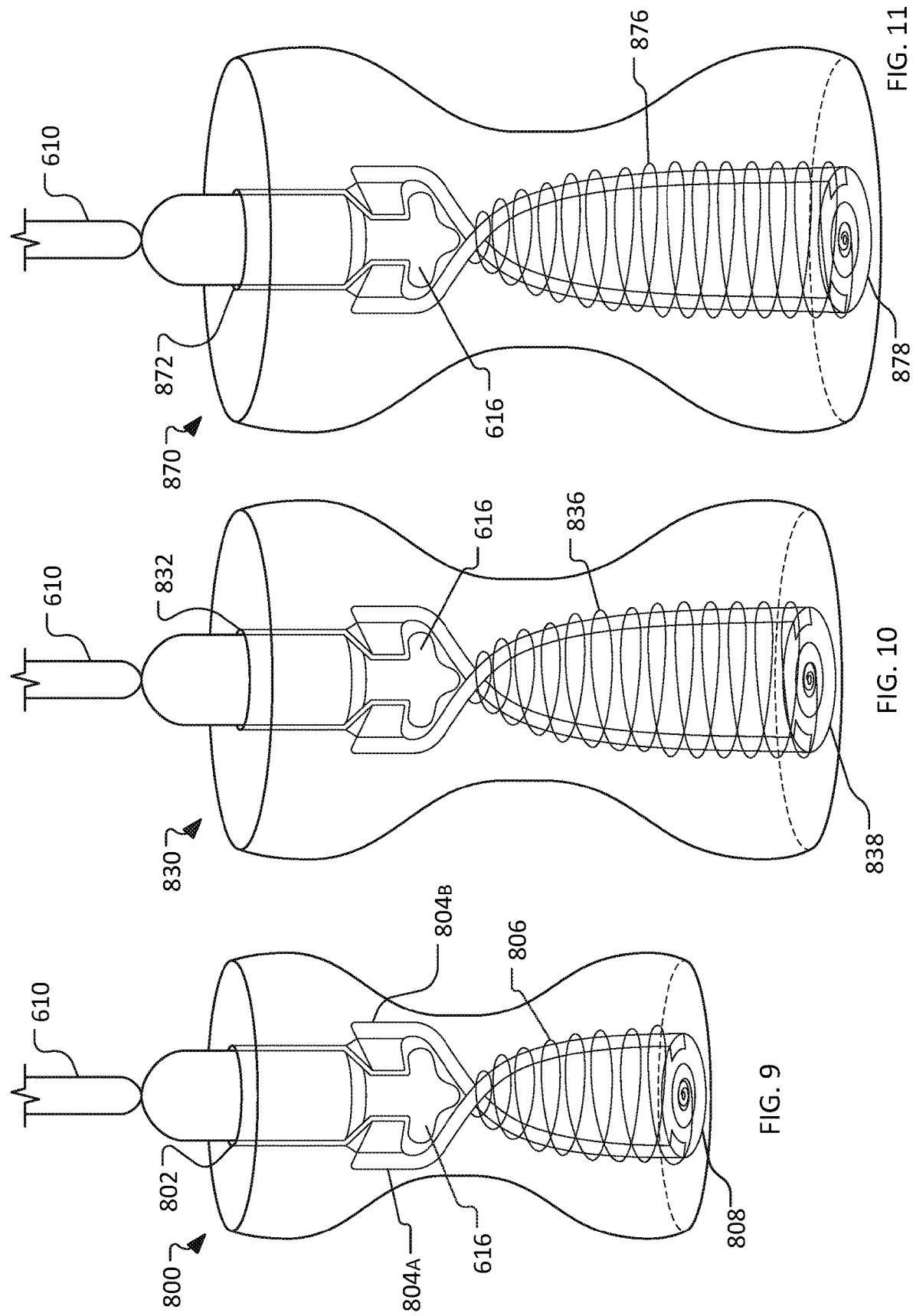

WEIGHTED SURGICAL RETRACTOR SYSTEMS

CROSS-REFERENCE TO RELATED APPLICATIONS

This application is a continuation of U.S. application Ser. No. 15/122,504, filed Aug. 30, 2016, which is a National Stage application under 35 U.S.C. § 371 of International Application No. PCT/US2015/018977, having an International Filing Date of Mar. 5, 2015, which claims the benefit of U.S. Provisional Application Ser. No. 61/949,521, filed Mar. 7, 2014. The disclosure of the prior applications are considered part of (and are incorporated by reference in) the disclosure of this application.

BACKGROUND

1. Technical Field

This document relates to surgical retractor devices and systems. For example, this document relates to a weighted surgical retractor system.

2. Background Information

Surgical retractors are used for grasping, retaining, or holding back tissue during surgery procedures so that body parts that would otherwise be blocked by the tissue may be accessed. Retractors play an important role during surgery, as they ensure that there is a clear view of the surgical site, and also help keep the tissues being retracted from being damaged. Some retractors are stainless steel tools possessing a curved, hooked, or angled blade fitted with a handle such that the retractor is handheld during the surgery. While handheld surgical retractors may provide convenience of use in some situations, users of handheld surgical retractors may experience fatigue and discomfort when using the retractor for required periods of time. In addition, handheld surgical retractors inconveniently require utilization of the hand of a user that could otherwise be put to other more beneficial uses during a surgery.

SUMMARY

This document provides surgical retractor devices and systems. For example, this document provides a weighted surgical retractor system. In one example embodiment, this document provides a weighted Deaver retractor system that includes a selectable amount of weight that can be releasably coupled to a shaft of the retractor.

In general, one aspect of this document features a surgical retractor system. The surgical retractor system comprises a retractor shaft member, and one or more weight members that are configured to be releasably coupled to the retractor shaft member at the proximal weighted end. The retractor shaft member includes a distal working end and a proximal weighted end.

In some implementations of the surgical retractor system, the distal working end includes a roughened surface that is configured to have a higher coefficient of friction between the roughened surface and tissue of a patient than are other surfaces of the retractor shaft member. Optionally, the distal working end includes a portion that is concaved. In some implementations, the concaved portion includes a roughened surface that is configured to have a higher coefficient of friction between the roughened surface and tissue of a patient than are other surfaces of the retractor shaft member.

The distal working end may optionally include a kidney-shaped portion. In some embodiments, the kidney-shaped portion includes a roughened surface that is configured to have a higher coefficient of friction between the roughened surface and tissue of a patient than are other surfaces of the retractor shaft member. The surgical retractor system may further comprise a base weight member that is fixed to the retractor shaft member. In some embodiments, the one or more weight members are configured to releasably couple to the base weight member. In particular embodiments, the one or more weight members comprise at least two separate weight members. Optionally, the at least two separate weight members are configured to releasably couple to each other. Optionally, the one or more weight members comprise at least three separate weight members. In some embodiments, the at least three separate weight members are configured to releasably couple to each other. In particular embodiments, the distal working end is configured to be separable from the retractor shaft member. Optionally, the distal working end includes at least three retractor arms. In some embodiments, two of the at least three retractor arms are configured to deliver lateral retraction. In some embodiments, a portion of the distal end portion of the retractor shaft member may have scalloped lateral sides. Optionally, the surgical retractor system may further comprise a light source that is coupleable to the retractor shaft member.

Particular embodiments of the subject matter described in this document can be implemented to realize one or more of the following advantages. The performance of some surgical procedures can be enhanced using the weighted surgical retractors provided herein. In some cases, use of the weighted retractors provided herein can reduce fatigue and discomfort of clinicians that would otherwise be required to provide manual force while using a handheld retractor. In some embodiments, the amount of weight used with the weighted retractors provided herein is selectable by the clinician users, so as to suit the needs of a variety of patients, procedure types, and clinician's preferences. In some embodiments, a combination of downward and lateral retraction is provided by the surgical retractor devices provided herein. In particular embodiments, the surgical retractors provided herein are modular such that a variety of different types of working ends can be installed on a retractor shaft so as to suit a particular circumstance or user preference.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 1A is a perspective view of a weighted surgical retractor in accordance with some embodiments provided herein.

FIG. 1B illustrates an optional textured surface that is included on the working end of some embodiments of the weighted surgical retractors provided herein.

FIGS. 9-11 are perspective views of weights that can be used with some embodiments of the weighted surgical retractors provided herein.

Like reference numbers represent corresponding parts throughout.

DETAILED DESCRIPTION

Figure 2A:
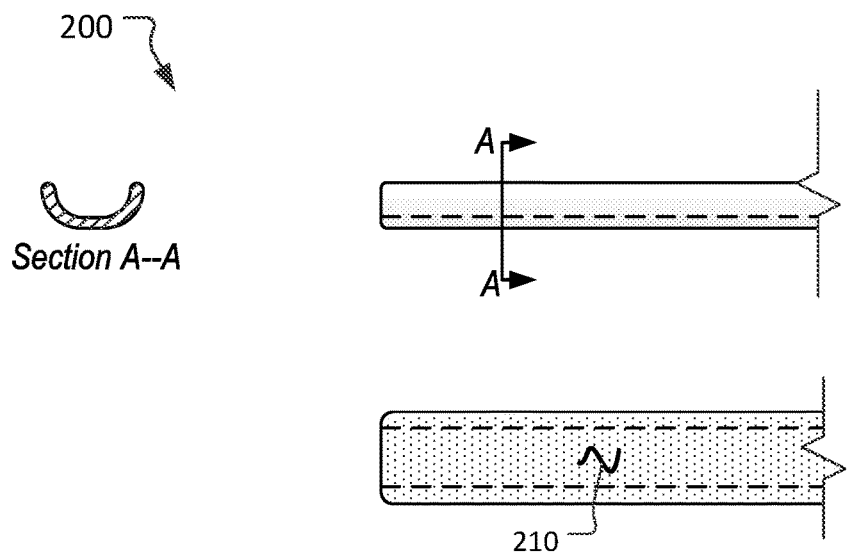
FIG. 2A illustrates side, bottom, and cross-sectional views of a concaved working end that is included in some embodiments of the weighted surgical retractors provided herein.

This document provides surgical retractor devices and systems. For example, this document provides a weighted surgical retractor system. In one example embodiment, this document provides a weighted Deaver retractor system that includes a selectable amount of weight that can be releasably coupled to a shaft of the retractor. The surgical retractors provided herein can be used during a variety of surgical procedures, including surgical procedures performed on the abdomen, thoracic regions, limbs, and so on. In some embodiments, the surgical retractors provided herein are well-suited for retraction of the vaginal canal for hysterectomy surgery, and for other procedures for which vaginal retraction is necessary.

In some embodiments, the surgical retractors provided herein are weighted retractors. In some such embodiments, the weighted portion of the surgical retractor is located at the proximal end of the retractor. In particular embodiments, the weighting of the retractors is selectively adjustable by a clinician using the weighted retractor. Such weight adjustments can be made at any time before or during a surgical procedure. For example, as described further herein, the surgical retractors allow for additional weight to be incrementally added or removed as desired by the clinician. In this manner, the clinician can advantageously select a total weight of the retractor for a particular usage. Also, the clinician can thereby conveniently customize the weighted retractors provided herein, so as to function as desired over a broad range of applications, patients, conditions, and the like.

A variety of types of retractor working ends (also referred to herein as the "distal end") can be advantageously included with the weighted retractors provided herein. The retractor working ends can have various shapes and configurations, including but not limited to, concave, kidney-shaped, flanged, radiused, flared, curved, and so on. In addition, surfaces of the retractor working ends can be adapted to increase the friction between the retractor working ends and the tissue of a patient. In some embodiments, such surfaces can be textured by knurling or checkering (to create a diamond pattern, angled pattern, straight pattern, etc.), stippling, dimpling, engraving, sandblasting, chemical etching, and so on. Further, in some embodiments, the working ends of the retractors provided herein can include extendable and retractable portions. The extendable portions can be used, for example, to customize the retractor for a particular surgical use or for the specific anatomy of a particular patient. In some embodiments, the extendable portions can add to the distal length of the retractor. In some embodiments, the extendable portions can add to the width of the working end of the retractor.

With reference to FIG. 1A, an example weighted surgical retractor 100 includes a distal working end 110, a weighted end 120, and a retractor shaft member 130. In this embodiment, working end 110 is confluent with shaft member 130. At weighted end 120, in some embodiments shaft member 130 can be fixedly coupled with a base weight member 122 and selectively releasably coupled with one or more supplemental weight members 124a-c. The configuration of weighted end 120 will be described further herein, for example in reference to FIGS. 3, 4, and 5A-5C.

Weighted surgical retractor 100 is an example of a Deaver style of retractor. It should be understood that the concepts described herein can also be applied to many other types of surgical retractors, in addition to Deaver retractors.

The material from which shaft member 130 and, in this embodiment, working end 110 are made can include any suitable metal, metal alloy, polymer, and combinations thereof. In some embodiments, the material of shaft member 130 and working end 110 are a stainless steel, such as surgical grade 402 stainless steel. In alternative embodiments, polymers such as thermoplastic or thermoset polymers can be used. Two polymeric materials which can be suitable are polyetherimide and polyimide. In some embodiments, liquid crystal polymers can also be used. Such metallic and polymeric materials can allow for repeated sterilization and reuse of retractors in some circumstances.

The material used for shaft members and working ends can be formed, machined, molded, etc., to create the physical features desired. For example, shaft members and working ends can be shaped to include curved, angled, narrowed, widened, thickened, and thinned portions, to provide a few examples. In the depicted embodiment, shaft member 130 is a strip of 402 stainless steel that has been formed by bending to include multiple curvatures to create a retractor style that is known in the art as a Deaver retractor. Working end 110 has been formed to include rounded corners and an upward bend at a distal tip 112 starting at about 2.5 centimeters from distal tip 112.

In some embodiments, some or all of the working end of a weighted retractor can include a textured surface that is configured to have an increased coefficient of friction in relation to body tissue, while not inflicting harm to the tissue. For example, with reference to FIG. 1B, working end 110 includes a textured surface 114. FIG. 1B provides a view of the underside (also referred to herein as "backside") of a distal-most portion of working end 110. As described previously, the texturing can be of various styles and forms. In the depicted embodiment, cross-hatching has been cut into the material of shaft member 130 at working end 110. Textured surface 114 is generally rectangular, and extends about 11.5 centimeters in length and the full width of shaft member 130. In other weighted retractor embodiments, textured surfaces can be larger, smaller, have various shapes or contours, and multiple discreet textured surfaces at differing locations on the working end may be included.

Referring again to FIG. 1A, a range of sizes of shaft members and working ends of the weighted surgical retractors provided herein are envisioned (such as is typical in the art). In the depicted example embodiment, weighted retractor 100 is made from a strip of 402 stainless steel material that is about 40 centimeters long, about 2 centimeters wide, and about 5 millimeters thick. Shaft member 130 includes a generally semi-circular portion 132. In this embodiment, the diameter of semi-circular portion 132 is about 10 centimeters. Near weighted end 120, a generally linear shaft portion 134 that is at least about 5 centimeters in length is included. Such dimensions are provided by way of example, and not as limitations.

As described further herein (e.g., in reference to FIGS. 3, 4, and 5A-5C), shaft member 130 can be fixedly coupled with base weight member 122 at weighted end 120. In alternative embodiments, all weight members, including a base weight, can be decoupled from the shaft member, such that in certain circumstances no weights are included. Supplemental weight members 124a-c can be selectively releasably coupled with shaft member 130. For example, if the clinician user desires more weight than is provided by base weight member 122 alone, the clinician can couple a first supplemental weight member 124a to shaft portion 134. If the clinician desires still more weight, the clinician can couple a second supplemental weight member 124b to shaft portion 134. Similarly, a third supplemental weight member 124c can be coupled to shaft portion 134. In some embodiments of weighted retractors, more than three supplemental weight members can be selectively coupled to the shaft member. For example, in some embodiments four, five, six, or more than six supplemental weight members can be selectively coupled to the shaft member.

In some embodiments, each of the supplemental weight members of a weighted retractor system has the same weight. For example, the supplemental weight members of a particular weighted retractor system may each equally weigh about 1.1 kilograms, about 2.2 kilograms, about 4.4 kilograms, about 6.6 kilograms, about 8.8 kilograms, or more than 8.8 kilograms. In alternative embodiments, the supplemental weight members of a particular weighted retractor system may include a variety of two or more different weights, such as weights of about 1.1 kilograms, about 2.2 kilograms, about 4.4 kilograms, about 6.6 kilograms, about 8.8 kilograms, or more than 8.8 kilograms.

With reference to FIG. 2A, an embodiment of a distal working end 200 that can be incorporated with the weighted retractors provided herein is illustrated. Working end 200 is an example of a concaved distal end. That is, working end 200 is shaped as a channel, as best seen in section A-A. The concaved shape can be advantageous in some circumstances. For example, in some cases the shape can tend to conform with the tissue with which working end 200 makes contact. The shape can also allow for enhanced visualization of the surgical field and for improved access by other surgical tools in some situations.

The backside of working end 200 includes an optional roughened region 210. As described previously, roughened region 210 can be of various styles and forms. In the depicted embodiment, stippling has been formed into the material of working end 200. Roughened region 210 is on the convex side of working end 200, including on the sides that extend generally parallel to each other. In other weighted retractor embodiments, textured surfaces can be larger, smaller, have various shapes, and multiple discreet textured surfaces at differing locations may be included.

Figure 2B:
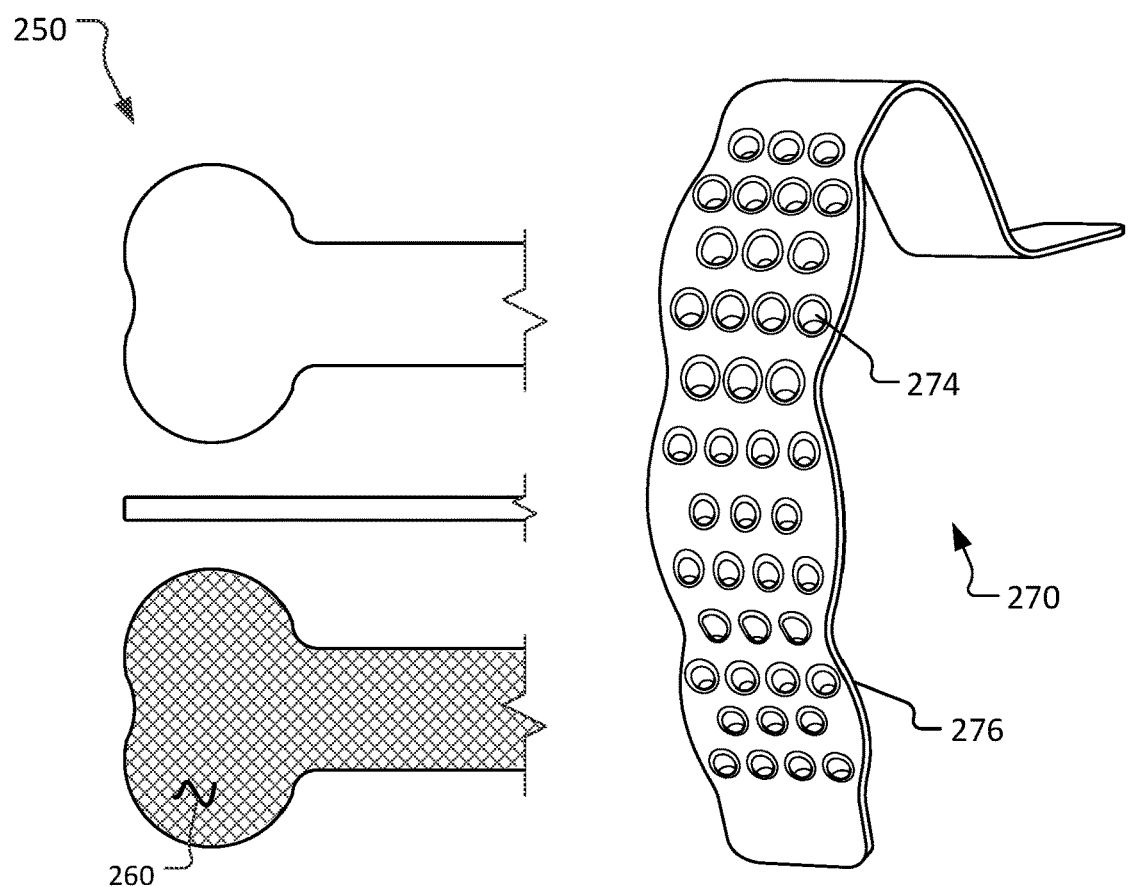
FIG. 2B illustrates side, top, and bottom views of a kidney-shaped working end that is included in some embodiments of the weighted surgical retractors provided herein.

With reference to FIG. 2B, another embodiment of a distal working end 250 that can be incorporated with the weighted retractors provided herein is illustrated. Working end 200 is an example of a kidney-shaped working end. Kidney-shaped working end 250 can be advantageous in some circumstances. For example, the shape can tend to retract a larger surface area of tissue with which working end 250 makes contact, as compared to some other shapes. The shape can also allow for enhanced visualization of the surgical field and for improved access by other surgical tools in some situations.

The backside of working end 250 includes an optional roughened region 260. As described previously, roughened region 260 can be of various styles and forms. In the depicted embodiment, a knurled pattern has been formed into one side of the material of working end 250. In some embodiments, roughened region 260 can enhance the ability of a retractor to grip tissue, while not damaging tissue. In other weighted retractor embodiments, textured surfaces can be larger, smaller, have various shapes, and multiple discreet textured surfaces at differing locations may be included.

Figure 2C:
FIG. 2C is a perspective view of another embodiment of working end that is included in some embodiments of the weighted surgical retractors provided herein.

FIG. 2C provides another embodiment of a working end 270 that is included in some embodiments of the weighted surgical retractors provided herein. In some embodiments, working end 270 is made of surgical stainless steel, or another type of biocompatible metallic material or polymeric material. Working end 270 includes a textured surface that is created in this example by a plurality of protrusions 274 on the underside of working end 270 (visible in FIG. 2C as indentations on the outside of working end 270). Working end 270 also includes scalloped lateral edges 276.

Figure 3:
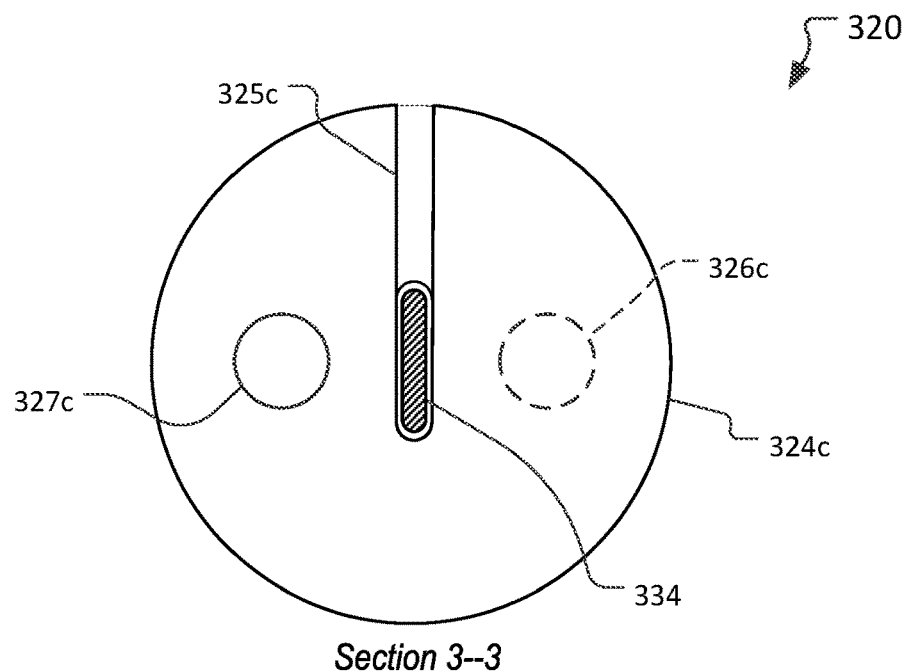
FIG. 3 illustrates a top cross-sectional view and side exploded view of a weight arrangement that is included in some embodiments of the weighted surgical retractors provided herein.
Figure 3:
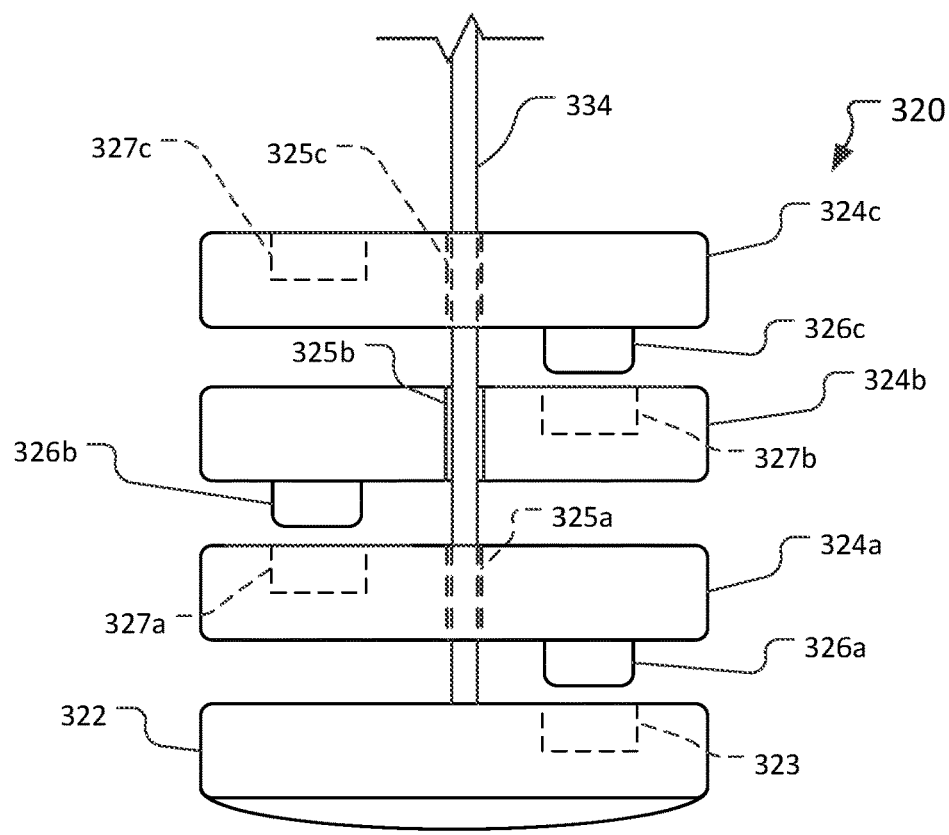

With reference to FIG. 3, a weighted end 320 is depicted that can be used with some embodiments of the weighted retractors provided herein. The upper view is a sectional view corresponding with FIG. 1A. The lower view is an exploded view that illustrates surface features of the individual weights that can be selectively added to weighted end 320.

Weighted end 320 includes a generally linear shaft portion 334, a base weight member 322, and one or more supplemental weight members 324a-c. In this embodiment, three supplemental weight members 324a-c are included, but in other embodiments, more or fewer supplemental weight members can be included. Shaft portion 334 can be fixedly coupled with base weight member 322. In other embodiments, all weight members can be uncoupled from the retractor shaft.

The weight members 322 and 324a-c (and other weight members described herein) can be made from a variety of materials. In some embodiments, relatively dense materials, such as metals, are used. For example, stainless steel materials can be used in some embodiments. A 304 stainless steel is one example material that can be used. Plated metals (e.g., chrome or nickel plating) can be used in some embodiments. While weight members 322 and 324a-c are depicted as cylindrical, it should be understood that a cylindrical shape is not required. In some embodiments, other shapes are used, such as square, rectangular, ovular, shapes that are ergonomically shaped for grasping, and the like.

Supplemental weight members 324a-c can be selectively releasably coupled with shaft portion 334. In this embodiment, each supplemental weight member 324a-c has a slot 325a-c that is slightly wider than shaft portion 334. Accordingly, shaft portion 334 can be slid within slots 325a-c of supplemental weight members 324a-c to selectively couple supplemental weight members 324a-c with shaft portion 334. In some embodiments, a thumb screw (or similar mechanical coupling mechanisms) can be included to enhance the fixation between shaft portion 334 and supplemental weight members 324a-c. In particular embodiments, a quick-connect type of connector can be used to couple supplemental weight members 324a-c to shaft portion 334. In some such embodiments, a push button can be used to decouple supplemental weight members 324a-c from shaft portion 334.

Supplemental weight members 324a-c can also couple with each other or with base weight member 322. For example, supplemental weight member 324a includes a protrusion 326a that projects into a complementary hole 323 of base weight member 322. A close slip fit can be used between protrusion 326a and hole 323. Accordingly, supplemental weight member 324a can be selectively releasably coupled with base weight member 322. Supplemental weight member 324b can, in turn, be selectively coupled with supplemental weight member 324a. For example, supplemental weight member 324b can include a protrusion 326b that can project into a hole 327a of supplemental weight member 324a. Likewise, supplemental weight member 324c can include a protrusion 326c that can project into a hole 327b of supplemental weight member 324b. In this fashion, a stack of supplemental weight members 324a-c (or fewer or more, in other embodiments) can be added to weighted end 320 in a manner by which supplemental weight members 324a-c are functionally coupled to shaft portion 334 and to each other.

While this embodiment uses protrusions and complementary holes, other kinds of features can be incorporated to releasably couple supplemental weight members to a retractor shaft and to each other. For example, ridges and corresponding slots can be used. In another example, cone-shaped protrusions and receptacles can be used. Set screws can be used to attach the weights to the retractor shaft. Further, in some embodiments magnetic attraction between supplemental weights can be incorporated to releasably couple supplemental weight members to a retractor shaft and to each other. In another embodiment, suction cups can be used. In another embodiment, high-friction (e.g., rubberized) sheet material can be used between the supplemental weight members to provide frictional coupling therebetween. These and other like features, and combinations of such features, can be used to releasably couple supplemental weight members to a retractor shaft and to each other.

Figure 4:
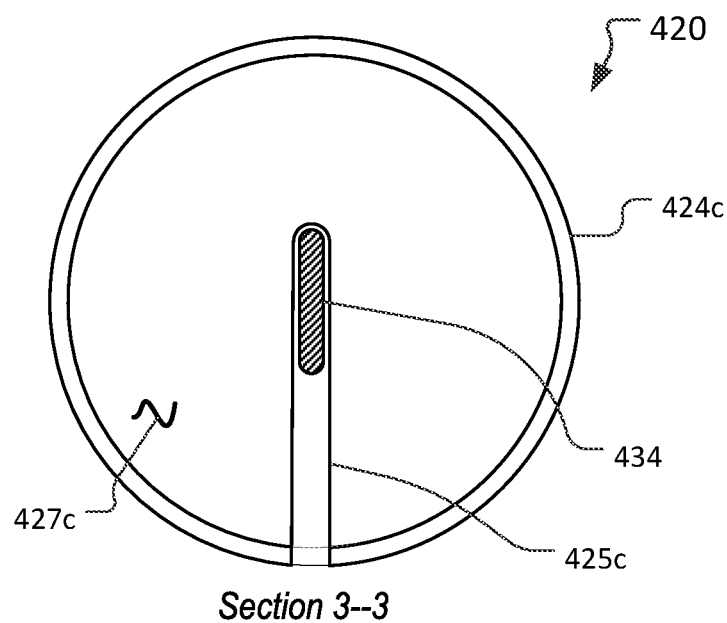
FIG. 4 illustrates a top cross-sectional view and side exploded view of another weight arrangement that is included in some embodiments of the weighted surgical retractors provided herein.
Figure 4:
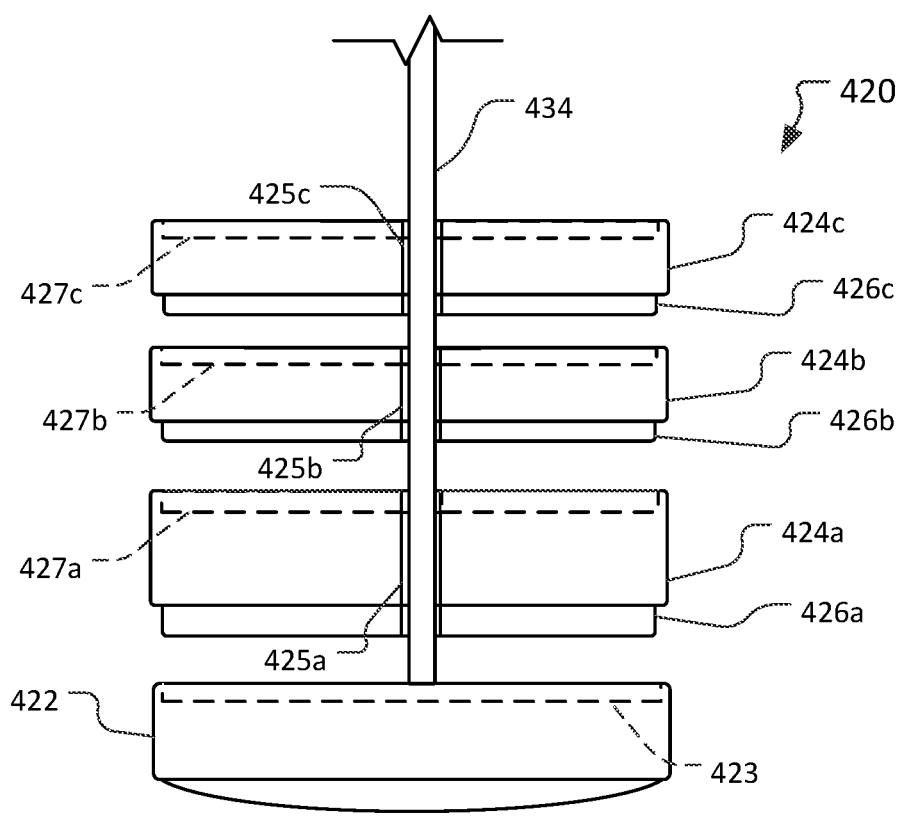

With reference to FIG. 4, a weighted end 420 can be used with some embodiments of the weighted retractors provided herein. The upper view is a sectional view corresponding with FIG. 1A. The lower view is an exploded view that illustrates surface features of the individual weights that can be selectively added to weighted end 420.

Weighted end 420 includes a generally linear shaft portion 434, a base weight member 422, and one or more supplemental weight members 424a-c. In this embodiment, three supplemental weight members 424a-c are included, but in other embodiments, more or fewer supplemental weight members can be included. Shaft portion 434 can be fixedly coupled with base weight member 422. In other embodiments, all weight members can be uncoupled from the retractor shaft.

Supplemental weight members 424a-c can be selectively releasably coupled with shaft portion 434. In this embodiment, each supplemental weight member 424a-c has a slot 425a-c that is slightly wider than shaft portion 434. Accordingly, shaft portion 434 can be slid within slots 425a-c of supplemental weight members 424a-c to selectively couple supplemental weight members 424a-c with shaft portion 434. In some embodiments, a set screw, spring pin, spring-loaded detent ball, or similar mechanical coupling mechanisms, can be included to enhance the fixation between shaft portion 434 and supplemental weight members 424a-c. In particular embodiments, a quick-connect type of connector can be used to couple supplemental weight members 424a-c to shaft portion 434. In some such embodiments, a push button can be used to decouple supplemental weight members 424a-c from shaft portion 434.

Supplemental weight members 424a-c can also couple with each other, or with base weight member 422. For example, supplemental weight member 424a includes a protrusion 426a that projects into a complementary receptacle 423 of base weight member 422. A close slip fit can be used between protrusion 426a and receptacle 423. Accordingly, supplemental weight member 424a can be selectively releasably coupled with base weight member 422. Supplemental weight member 424b can, in turn, be selectively coupled with supplemental weight member 424a. For example, supplemental weight member 424b can include a protrusion 426b that can project into a receptacle 427a of supplemental weight member 424a. Likewise, supplemental weight member 424c can include a protrusion 426c that can project into a receptacle 427b of supplemental weight member 424b. In this fashion, a stack of supplemental weight members 424a-c (or fewer, or more) can be added to weighted end 420 in a manner by which supplemental weight members 424a-c are functionally coupled to shaft portion 434 and to each other.

Figure 5C:
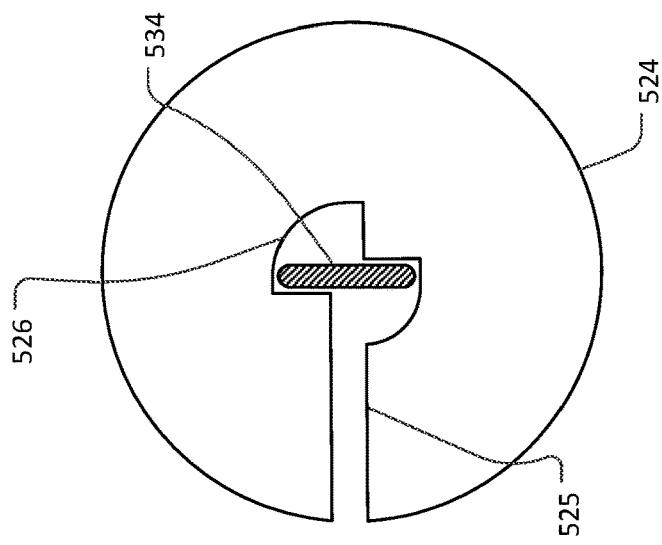
FIGS. 5A-5C are a sequence of figures that illustrate the coupling of a weight to the shaft of a retractor using an example configuration whereby weights can be releasably coupled to the retractor shaft.
Figure 5B:
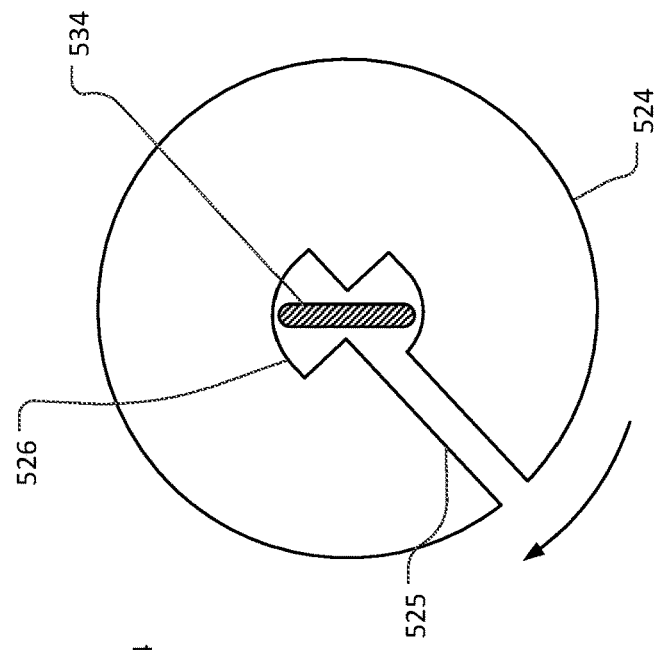
Figure 5A:
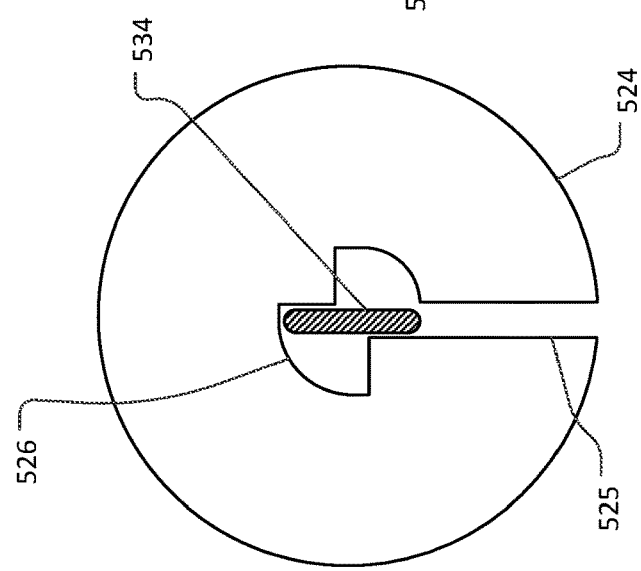

With reference to FIGS. 5A-5C, another example mechanical technique for coupling weight members to a retractor shaft is provided. These figures provide a sequential representation of the coupling process, beginning with FIG. 5A and ending with FIG. 5C (whereat the coupling is complete).

FIG. 5A illustrates a cross-sectional view of a retractor shaft member 534 and a top view of a weight member 524. Weight member 524 includes a slot 525 and a bore 526. Bore 526 is configured so that weight member 524 can be rotated 90 degrees (see FIG. 5B) to arrive at a coupled arrangement as depicted in FIG. 5C. In the arrangement of FIG. 5C, weight member 524 is coupled with shaft member 534 such that weight member 524 must be rotated to become uncoupled from shaft member 534. When this type of mechanical technique for coupling weight members to a retractor shaft is used, other additional coupling features (e.g., protrusions and complementary holes as described elsewhere herein) can be optionally included, or not included.

Figure 6:
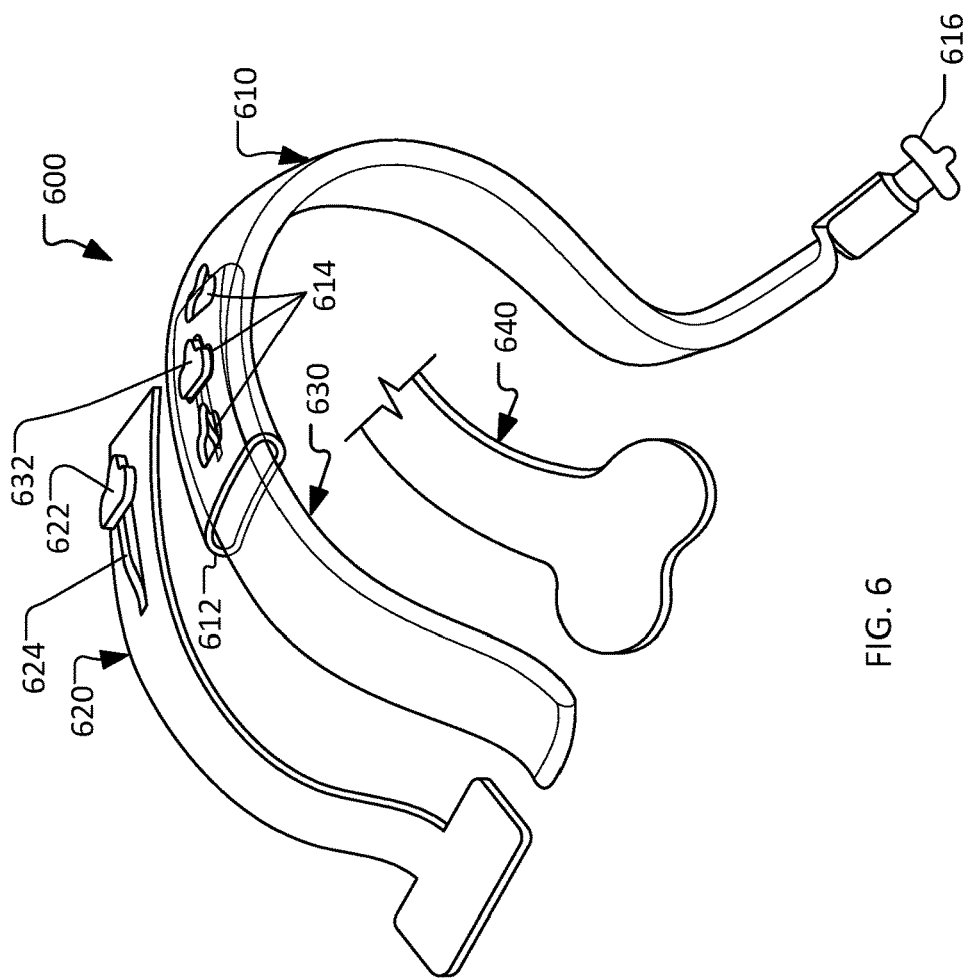
FIG. 6 is a perspective view of a modular weighted retractor in accordance with some embodiments provided herein.

Referring now to FIG. 6, the embodiments of surgical retractors provided herein include example modular weighted retractor 600. Modular weighted retractor 600 includes a retractor shaft 610, and one or more working ends 620, 630, and 640 that are releasably coupleable with retractor shaft 610. Modular weighted retractor 600 also includes at least one weight (e.g., as will be described further in reference to FIG. 8, or other types of weights as described herein). Retractor shaft 610 includes a male end 616 that can be used to releasably couple a weight to retractor shaft 610, as will be described further in reference to FIG. 8.

The working ends of modular weighted retractor 600 can be configured in virtually any style as desired. For example, FIG. 6 provides three non-limiting example working ends: (1) a T-shape working end 620, (2) a Deaver-type working end 630, and (3) a kidney-shape working end 640. Other types of working ends are also envisioned within the scope of this disclosure, such as, but not limited to, scalloped-sided working ends (e.g., refer to FIG. 2C).

Working ends 620, 630, or 640 can be releasably coupled to retractor shaft 610. In other words, a particular working end can be coupled to retractor shaft 610, then later uncoupled from retractor shaft 610 and a different working end can be coupled to retractor shaft 610. In other words, working ends 620, 630, and 640 are interchangeably coupleable with retractor shaft 610. Accordingly, modular weighted retractor 600 provides a flexibly designed retractor system that can be configured as desired by a clinician operator to suit a particular clinical need.

With a working end coupled to retractor shaft 610, modular weighted retractor 600 is a complete retractor assembly that is configured for use (with the exception, perhaps, of attaching a weight as will be described further below). For example, Deaver-type working end 630 is shown coupled together with retractor shaft 610. That assembly of Deaver-type working end 630 and retractor shaft 610 is configured for use because working end 630 is coupled with retractor shaft 610.

Various coupling techniques and mechanisms can be used to releasably couple working ends 620, 630, or 640 to retractor shaft 610. In the depicted embodiment, a distal end portion 612 of retractor shaft 610 is hollow so as to slidably receive a portion of working ends 620, 630, or 640 therein. Working ends 620, 630, and 640 each include a physical feature for coupling with retractor shaft 610. For example, in the depicted embodiments the physical feature for coupling with retractor shaft 610 is a male detent member 622 on working end 620 and male detent member 632 on working end 630. Working end 640 also includes a male detent member, but only the distal end portion of working end 640 is shown, to keep FIG. 6 clear and uncluttered.

In the depicted embodiment, male detent members 622 and 632 are spring biased to protrude away from working ends 620 and 630. For example, a leaf spring 624 provides a spring force that biases male detent member 622 outward from working end 620. In other embodiments, other types of springs or other biasing mechanisms can be utilized.

When a user of modular weighted retractor 600 wants to couple a particular working end to retractor shaft 610, the user can manually depress the male detent member of the particular working end and then slide a proximal end portion of the particular working end into distal end portion 612 of retractor shaft 610. For example, male detent member 632 of Deaver-type working end 630 can be depressed and slid into distal end portion 612 of retractor shaft 610, as depicted in FIG. 6.

As the working end is being slid into retractor shaft 610, the male detent member will encounter one or more openings 614, which are configured to allow the male detent member to protrude therethrough. For example, retractor shaft 610 includes three openings 614 that are spaced apart from each other. In the depicted configuration, male detent member 632 of Deaver-type working end 630 is protruding from the middle opening of the three openings 614 of retractor shaft 610. In this configuration (where the male detent member 632 is protruding from an opening 614 in the retractor shaft 610), working end 630 and retractor shaft 610 are coupled together. Having multiple openings 614 in retractor shaft 610 allows the user to adjust the length of the exposed portion of the working end 630. In some embodiments, openings 614 are spaced about 1.0 inch apart from each other. But, in other embodiments other increments that are closer to each other or further apart from each other can be used.

Still referring to FIG. 6, to uncouple working end 630 from retractor shaft 610, the user can manually depress male detent member 632 and slide working end 630 away from retractor shaft 610. In the process of sliding working end 630 away from retractor shaft 610, male detent member 632 may need to be depressed one or more additional times if male detent member 632 encounters additional openings 614 prior to a total separation of working end 630 from retractor shaft 610.

While the coupling mechanism of the depicted embodiment has been fully described, it should be understood that other types of coupling techniques and mechanisms are also envisioned within the scope of this disclosure. For example, such coupling mechanisms may include, but are not limited to, threaded couplings, telescoping arrangements, magnetic couplings, ratcheting couplings, and the like, and combinations thereof.

In some embodiments, working ends 620, 630, and 640 can be one-time-use disposable items. In some embodiments, working ends 620, 630, and 640 can be resterilizable and reusable. In particular embodiments, working ends 620, 630, and 640 are plastic-coated. Working ends 620, 630, and 640 may also be malleable, or may have portions that are malleable in some embodiments. For example, in the depicted embodiments, at least a distal end portion of working ends 620, 630, and 640 are malleable.

While distal end portion 612 of retractor shaft 610 is depicted as having smooth and generally linear lateral side surfaces, in some embodiments the lateral side surfaces of distal end portion 612 are scalloped. For example, the lateral side surfaces of distal end portion 612 may be scalloped (e.g., with wavy or undulating lateral side surfaces as exemplified by scalloped lateral edges 276 in FIG. 2C). In some embodiments, the extent or length of the scalloped distal end portion 612 corresponds to about the region that includes openings 614. In some embodiments, the length of the scalloped distal end portion 612 corresponds to the portion of working end 270 depicted by scalloped lateral edges 276 (refer to FIG. 2C). While in some embodiments the lateral side surfaces of distal end portion 612 may be scalloped, nevertheless working ends 620, 630, and 640 can be slidably received therein.

Figure 7:
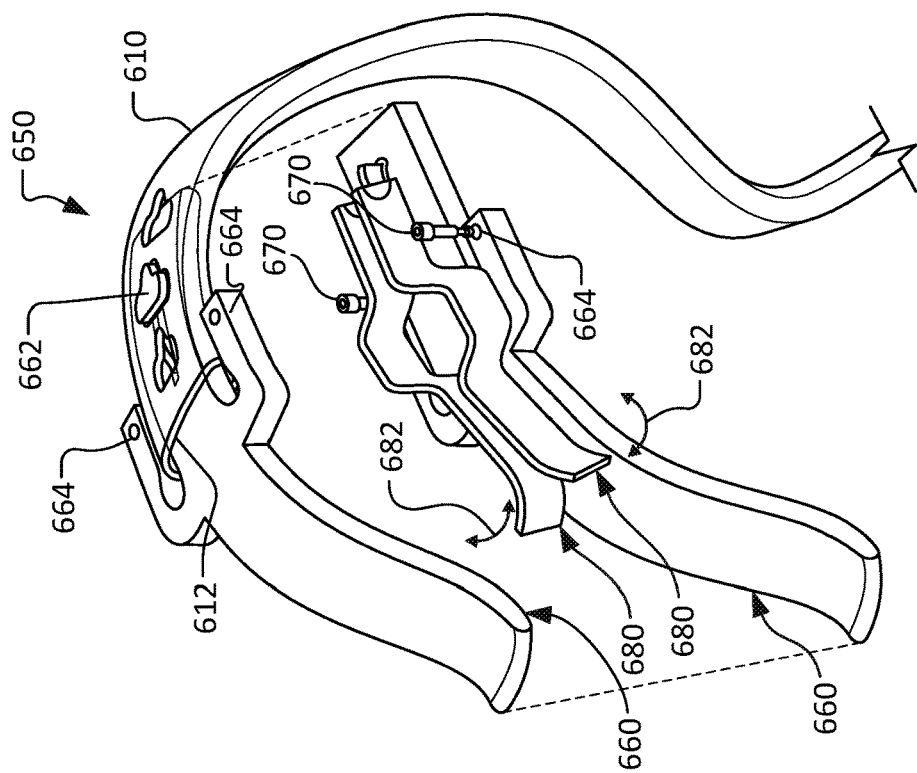
FIG. 7 is a perspective view of another modular weighted retractor in accordance with some embodiments provided herein.

FIG. 7, provides another example modular weighted retractor 650 in accordance with some embodiments provided herein. Modular weighted retractor 650 includes retractor shaft 610 (as described above) and a working end 660 that can receive additional attachments thereto. For example, in the depicted embodiment, two lateral retractor arms 680 are attached to working end 660. Lateral retractor arms 680 provide the capability to retract tissue in a direction that is lateral to the direction of the retraction provided by working end 660. For example, in one implementation, lateral retractor arms 680 can provide lateral vaginal retraction, while working end 660 retracts vaginal tissue posteriorly. But, it should be understood that modular weighted retractor 650 is not limited to such a use.

Working end 660 can be coupled to retractor shaft 610 by sliding a distal end portion of working end 660 into hollow distal end portion 612 of retractor shaft 610 as described above. Working end 660 can include any of the various types of ends as described elsewhere herein, e.g., Deavor-shape, kidney-shape, T-shape, concaved, and the like. Working end 660 can also include textures and can be malleable in some embodiments, and so on.

Working end 660 includes one or more attachment portions 664 to which other devices can be attached. For example, in the example embodiment attachment portions 664 are depicted as two holes that can receive two posts 670. In other embodiments, other types of attachment mechanisms can be used. In this embodiment, posts 670 can be used to couple lateral retractor arms 680 to working end 660.

In the illustrated embodiment, lateral retractor arms 680 are laterally pivotable in relation to working end 660, as depicted by arrows 682. The pivoting motion of lateral retractor arms 680 in relation to working end 660 can be facilitated by posts 670. In other words, in some embodiments lateral retractor arms 680 can pivot in relation to posts 670, while posts 670 are fixed in relation to working end 660. In alternative embodiments, lateral retractor arms 680 are fixed in relation to posts 670, and posts 670 (and lateral retractor arms 680) can pivot in relation to working end 660. In still other embodiments, both of the aforementioned pivoting arrangements can be included.

In some embodiments, the pivotable relationship between lateral retractor arms 680 and working end 660 includes a ratcheting mechanism. For example, in some embodiment posts 670 can include a ratchet mechanism. In such embodiments, a user can pivot lateral retractor arms 680 into a desired lateral position, and lateral retractor arms 680 will be detained approximately in the position. Such a feature can be used to maintain a laterally outward pressure by which tissue can be retracted laterally. In some embodiments, the ratcheting mechanism is a reversible mechanism. That is, the user can trip a lever and then the ratcheting mechanism will work in the reverse direction. In other embodiments, the ratcheting mechanism is a one-way mechanism. In some such embodiments, the ratcheting detent function can be released or reset by pivoting lateral retractor arms 680 to an end of travel location at which the ratcheting is released and then lateral retractor arms 680 can be pivoted inward.

In some embodiments, lateral retractor arms 680 can be malleable, or portions thereof can be malleable. As with other working ends described herein, lateral retractor arms 680 can have various forms, materials, surface textures, and the like.

Figure 8:
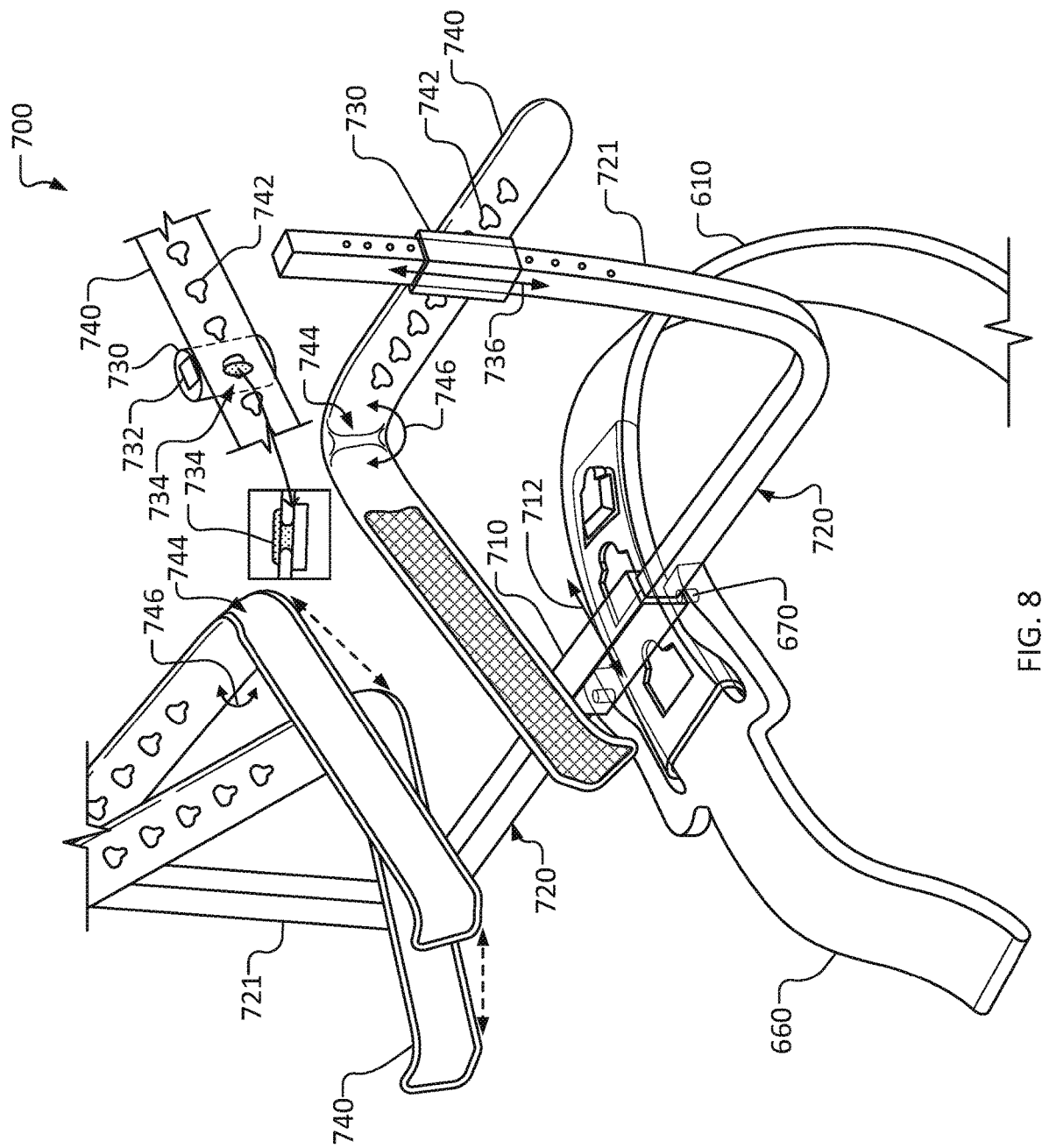
FIG. 8 is a perspective view of another modular weighted retractor in accordance with some embodiments provided herein.

Referring now to FIG. 8, another embodiment of a modular weighted retractor 700 is provided. Modular weighted retractor 700 includes retractor shaft 610 (as described above), working end 660 (as described above) and posts 670 (as described above). An articulating bar attachment 710 can be movably coupled to posts 670. Articulating bar attachment 710 receives a spring-type retractor frame 720. Attached to retractor frame 720 are two adjustable lateral retractor arms 740. Therefore, as with modular weighted retractor 650 of FIG. 7, modular weighted retractor 700 can provide lateral retraction as well as retraction from working end 660.

In some embodiments, articulating bar attachment 710 can be coupled with posts 670 so as to facilitate a position adjustment of articulating bar attachment 710 in relation to retractor shaft 610 as indicated by arrow 712.

Articulating bar attachment 710 can couple retractor frame 720 to working end 660. In the depicted embodiment, retractor frame 720 includes two upright portions 721. One lateral retractor arm hub 730 is slidably coupled to each of the two upright portions 721 (while one lateral retractor arm hub 730 is shown, the other lateral retractor arm hub 730 is not shown so as to simplify the illustration). Lateral retractor arm hubs 730 can slidingly translate in relation to upright portions 721 as indicated by arrow 736. Lateral retractor arm hubs 730 can be releasably detained (locked) in any position along the length of upright portions 721. In some embodiments, a spring-loaded ball detent mechanism can be used in conjunction with indentations on upright portions 721 to detain lateral retractor arms hubs 730 at certain positions on upright portions 721. In other embodiments, other types of locking or detent mechanisms can be used.

In the depicted embodiments, lateral retractor arm hubs 730 include a mushroom head-shaped protrusion 734. Protrusions 734 can releasably couple with keyhole-shaped clearance areas 742 of lateral retractor arms 740. Lateral retractor arms 740 can include multiple keyhole-shaped clearance areas 742 as shown. Accordingly, by selecting a particular keyhole-shaped clearance area 742 with which to couple mushroom head-shaped protrusion 734, the user can laterally adjust the position of lateral retractor arms 740 in relation to working end 660.

In some embodiments, lateral retractor arms 740 also include articulating joints 744. In some embodiments, articulating joints 744 are pivotable as indicated by arrows 746. In some embodiments, the pivoting of articulating joints 744 is facilitated by a ratchet mechanism. Accordingly, ratcheting articulating joints 744 can facilitate additional adjustments to the positions of lateral retractor arms 740 in relation to working end 660. In some cases, this type of adjustment may be known as "toeing in." In some embodiments, however, lateral retractor arms 740 are not articulated at the located indicated by the articulating joints 744. Rather, lateral retractor arms 740 are fixed and non-pivoting at that location in some embodiments.

Referring now to FIGS. 9-11, a one-pound weight 800, a two-pound weight 830, and a three-pound weight 870 are attachable to some embodiments of the weighted retractors provided herein. These example weights 800, 830, and 870 can be used with weighted retractors having any of the features as described above, such as the various types of working ends, textures, lateral retractors, malleability, modularity, and so on. Weights 800, 830, and 870 can be ergonomically shaped and contoured. The ergonomic shape can facilitate convenient and safe gripping and handling of weights 800, 830, and 870.

Other weight amounts are also envisioned in addition to the one, two, and three pound embodiments shown. For example, weights that are greater than three pounds, less than one pound, and weights having fractional amounts (e.g., 1.5 pounds, 2.5 pounds, and so on) are also envisioned.

The one-pound weight 800 of FIG. 9 will now be described in detail as an example. It should be understood that the description also applies to the two-pound weight 830 and the three-pound weight 870, inter alia.

Referring to FIG. 9, as described above some retractor shafts, such as retractor shaft 610, can include male end 616 (e.g., refer to FIG. 6). In these figures, weights 800, 830, and 870 are illustrated transparently so that the internal areas of weights 800, 830, and 870 can be envisioned. Male end 616 includes physical features that facilitate coupling retractor shaft 610 to weight 800. For example, to couple retractor shaft 610 to weight 800, male end 616 is inserted in an opening 802 at the top of weight 800. Inside of weight 800, a receptor mechanism (arms 804a-b, in this example) has physical features that are complementary with the physical features of male end 616. A spring 806 of receptor mechanism 804a-b biases receptor mechanism 804a-b to be coupled with male end 616. Accordingly, when male end 616 is inserted into weight 800 through opening 802, male end 616 can become releasably coupled with receptor mechanism 804a-b by simply inserting male end 616 to a sufficient depth within weight 800. For example, male end 616 of retractor shaft 610 can conveniently snap into a coupled arrangement with receptor mechanism 804a-b of weight 800.

Weights 800, 830, and 870 can also include a convenient detachment mechanism. For example, weight 800 includes a push button 808 on the bottom of weight 800 that is an example detachment mechanism. In this embodiment, when push button 808 is depressed, arms 804a-b are separated such that male end 616 is released from being coupled with arms 804a-b. By locating push button 808 on the bottom of weight, the chances of an accidental release of weight 800 from retractor shaft 610 can be reduced. In other embodiments, other types of detachment mechanisms can be used including, but not limited to, threaded connections, magnetic connections, cam lock levers, twist-lock arrangements, and the like.

A number of different embodiments of surgical retractor devices and systems have been described herein. It should be understood that any of the embodiments may also include other features combined therewith. Such features include, but are not limited to, lighting, cameras, working channels, irrigation lines, suction lines, and the like. For example, in some embodiments a light source such as a fiber optic light or LED light is attached to the retractor to illuminate an internal space of a patient (e.g., vaginal cavity, etc.). In some such embodiments, the light source is releasably attachable to the retractor.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A surgical retractor system comprising:
   a retractor shaft member, the retractor shaft member including a distal working end and a proximal weighted end;
   a base weight member that is fixed directly to the retractor shaft member at the proximal weighted end; and
   multiple weight members that are each shaped and sized to be: (i) stacked directly on the base weight member; (ii) stacked directly on each other; and (iii) releasably coupled directly to the retractor shaft member at the proximal weighted end,
   wherein each weight member of the multiple weight members comprises a protrusion and defines a hole, wherein the protrusions are sized and shaped to fit in the holes, and wherein stacking the multiple weight members directly on each other results in physical engagement of the protrusions in the holes of adjacent weight members of the stacked multiple weight members.

2. The surgical retractor system of claim 1, wherein the distal working end includes a roughened surface that is configured to have a higher coefficient of friction between the roughened surface and tissue of a patient than are other surfaces of the retractor shaft member.

3. The surgical retractor system of claim 1, wherein the distal working end includes a portion that is concaved.

4. The surgical retractor system of claim 3, wherein the concaved portion includes a roughened surface that is configured to have a higher coefficient of friction between the roughened surface and tissue of a patient than are other surfaces of the retractor shaft member.

5. The surgical retractor system of claim 1, wherein the distal working end includes a kidney-shaped portion.

6. The surgical retractor system of claim 5, wherein the kidney-shaped portion includes a roughened surface that is configured to have a higher coefficient of friction between the roughened surface and tissue of a patient than are other surfaces of the retractor shaft member.

7. The surgical retractor system of claim 1, wherein the distal working end of the retractor shaft member is releasably coupleable with a distal end portion of the retractor shaft member.

8. The surgical retractor system of claim 7, wherein the distal working end includes at least three retractor arms.

9. The surgical retractor system of claim 8, wherein two of the at least three retractor arms are configured to deliver lateral retraction.

10. The surgical retractor system of claim 7, wherein a portion of the distal end portion of the retractor shaft member has scalloped lateral sides.

11. The surgical retractor system of claim 1, further comprising a light source that is coupleable to the retractor shaft member.

12. The surgical retractor system of claim 1, wherein each weight member of the multiple weight members defines a slot that extends to a centrally located bore, wherein the slot is sized to slidably receive the retractor shaft member so that the retractor shaft member can be positioned in the centrally located bore, and wherein the centrally located bore is shaped to allow the weight member to be rotated about the retractor shaft member to radially lock the weight member onto the retractor shaft member while allowing longitudinal movement of the weight member relative to the retractor shaft member.

13. A surgical retractor system comprising:
a retractor shaft member, the retractor shaft member including a distal working end and a proximal weighted end;
a base weight member that is fixed directly to the retractor shaft member at the proximal weighted end; and
multiple weight members that are each shaped and sized to be: (i) stacked directly on the base weight member; (ii) stacked directly on each other; and (iii) releasably coupled directly to the retractor shaft member at the proximal weighted end,
wherein each weight member of the multiple weight members comprises a first side that has a protrusion and a second side that defines a receptacle that is sized and shaped to receive the protrusion, wherein the first and second sides of the multiple weight members are opposite sides, and wherein stacking the multiple weight members directly on each other results in physical engagement of the protrusions in the receptacles of adjacent weight members of the stacked multiple weight members.

14. The surgical retractor system of claim 13, wherein the distal working end includes a roughened surface that is configured to have a higher coefficient of friction between the roughened surface and tissue of a patient than are other surfaces of the retractor shaft member.

15. The surgical retractor system of claim 13, wherein the distal working end includes a portion that is concaved and has a roughened surface that is configured to have a higher coefficient of friction between the roughened surface and tissue of a patient than are other surfaces of the retractor shaft member.

16. The surgical retractor system of claim 13, wherein the distal working end includes a kidney-shaped portion, wherein the kidney-shaped portion includes a roughened surface that is configured to have a higher coefficient of friction between the roughened surface and tissue of a patient than are other surfaces of the retractor shaft member.

17. The surgical retractor system of claim 13, wherein the distal working end of the retractor shaft member is releasably coupleable with a distal end portion of the retractor shaft member, wherein the distal working end includes at least three retractor arms, wherein two of the at least three retractor arms are configured to deliver lateral retraction.

18. The surgical retractor system of claim 17, wherein a portion of the distal end portion of the retractor shaft member has scalloped lateral sides.

19. The surgical retractor system of claim 13, further comprising a light source that is coupleable to the retractor shaft member.

20. The surgical retractor system of claim 13, wherein each weight member of the multiple weight members defines a slot that extends to a centrally located bore, wherein the slot is sized to slidably receive the retractor shaft member so that the retractor shaft member can be positioned in the centrally located bore, and wherein the centrally located bore is shaped to allow the weight member to be rotated about the retractor shaft member to radially lock the weight member onto the retractor shaft member while allowing longitudinal movement of the weight member relative to the retractor shaft member.

* * * * *

UNITED STATES PATENT AND TRADEMARK OFFICE
CERTIFICATE OF CORRECTION

PATENT NO. : 11,666,316 B2
APPLICATION NO. : 16/721150
DATED : June 6, 2023
INVENTOR(S) : Timothy A. Harshman, Raymond Phelps and Steven Jurrens Page 1 of 1

It is certified that error appears in the above-identified patent and that said Letters Patent is hereby corrected as shown below:

On the Title Page

Column 1 (Item (71) Applicants), In Line 3, After (US); delete "Tara K. Phelps".

Signed and Sealed this
Twenty-sixth Day of November, 2024

Katherine Kelly Vidal
*Director of the United States Patent and Trademark Office*